US00RE38167E

(19) United States
(12) Reissued Patent
Brown et al.

(10) Patent Number: US RE38,167 E
(45) **Date of Reissued Patent: *Jul. 1, 2003**

(54) WEIGHT REDUCTION METHOD FOR CATS AND OTHER PETS

(75) Inventors: James H. Brown, Scottsdale, AZ (US); David R. Jones, Palm Beach, FL (US); Lon D. Lewis, Topeka, KS (US)

(73) Assignee: International Flora Technologies Ltd

( * ) Notice: This patent is subject to a terminal disclaimer.

(21) Appl. No.: 09/975,379

(22) Filed: Oct. 12, 2001

Related U.S. Patent Documents

Reissue of:
(64) Patent No.: 6,245,364
Issued: Jun. 12, 2001
Appl. No.: 09/372,941
Filed: Aug. 12, 1999

U.S. Applications:

(63) Continuation-in-part of application No. 08/608,766, filed on Feb. 29, 1996, now Pat. No. 5,962,043.

(51) Int. Cl.[7] ..... A23K 1/14; A23K 1/16; A23K 1/18

(52) U.S. Cl. ..... 426/2; 426/630; 426/635; 426/648; 426/805

(58) Field of Search ..... 426/2, 630, 635, 426/648, 805

(56) References Cited

U.S. PATENT DOCUMENTS 4,310,558 A * 1/1982 Nahns ..... 426/805
5,141,755 A * 8/1992 Weisman ..... 426/805

FOREIGN PATENT DOCUMENTS

WO 94/25035 * 11/1994

OTHER PUBLICATIONS

Manos CG, et al., *J. Agric Food Chem* 34:801–804 (1986).*

Arnouts S, et al., *Poultry Sci* 72: 1714–21 (1993).*

Cokelaere et al., Influence of Jojoba Meal Supplementation on Growth and Organ Function in Rats, *J Agric Food Chem*, vol. 40 1992, pp. 1444–1448 (1993).*

Cokelaere et al., Influence of Pure Simmondsin on the Food Intake in Rats, *J Agric Food Chem*, vol. 40, 1992, pp 1839–1842.*

Cokelaere et al, Fertility in Rats After Long–Term Jojoba Meal Supplementation, *Agric Food Chem.*, 1993, 41, 1449–1451.*

Cokelaere et al., Evidences for a Satiating Effect of Defatted Jojoba Meal, *Industrial Crops and Products* 4(1995) 91–96.*

* cited by examiner

*Primary Examiner*—Arthur L. Corbin
(74) *Attorney, Agent, or Firm*—The Halvorson Law Firm

(57) ABSTRACT

A pet food composition containing a small but sufficient amount of simmondsin component to provide a simmondsin activity within the range of 0.1% by weight of said pet food dry matter mix to about 1.5% by weight of said pet food dry matter mix. Also disclosed as part of the invention is a method of weight reduction of companion pets by adding pet food that contains the above-defined range of simmondsin activity contributed by a simmondsin component, simmondsin analogues or mixtures thereof, such as derived from defatted jojoba seed meal, and thereafter feeding the pet food to a companion pet on a regular and sustained basis until weight reduction occurs and then maintaining the pet's weight.

7 Claims, No Drawings

WEIGHT REDUCTION METHOD FOR CATS AND OTHER PETS

Matter enclosed in heavy brackets [ ] appears in the original patent but forms no part of this reissue specification; matter printed in italics indicates the additions made by reissue.

CROSS REFERENCE TO A RELATED APPLICATION

This application is a continuation-in-part of U.S. Ser. No. 08/606,766 filed Feb. 29, 1996, now U.S. Pat. No. 5,962, 043, the disclosure of which is hereby incorporated by reference.

BACKGROUND OF THE INVENTION

Obesity is the most common nutritional disease of companion pets such as dogs and cats in an affluent society. It in fact exceeds by far all deficiency diseases combined. Obesity generally is considered present when body weight of the companion pet is 15% or more greater than optimum, which is the point at which health problems begin increasing with increasing weight. It has, for example, been reported that in affluent societies from 24% to 44% of the dogs are obese. Generally speaking, the incidence of obesity in companion pets increases with the age of the pet. Similar to humans, as the animals age body fat increases, and the amount of lean body mass decreases. For dogs particularly, obesity is more common in female than males up to age 12 years.

Because obesity develops gradually, the companion pet owner is often unaware of the overweight condition until it is called to his or her attention. Rarely is an animal presented to a veterinarian solely for the problem of obesity, but instead because of dermatitis, shortness of breath, routine immunizations, or arthritic or rheumatic symptoms. It is not uncommon that obesity is the predisposing cause of the condition noticed by the owner, although the obesity itself may not be noticed. For example, in one study it was observed that nearly one-third of the owners of obese dogs did not realize that their dogs were overweight.

The cause of obesity in companion pets is quite simple—energy intake in excess of that utilized. However, the factors causing this are not quite so simple. Some dogs are known to be "easy keepers". That is, they become overweight while being fed commercial dog foods in amounts adequate for normal adult maintenance, and in the same amount and manner as their kennel mates who may maintain optimum weight.

In most instances, in companion pet obesity there are two stages—an initial phase and a static phase. The basic cause of the initial phase is a dietary energy intake in excess of that utilized, resulting in a positive energy balance which is deposited as fat. In the static phase, dietary intake is reduced in accordance with energy needs so that body weight remains constant in the obese state. Thus, the amount of food required to maintain the animal in obese state is no greater, and in fact is often less, than that required to maintain the normal, non-obese state.

Thus, the only successful way for reducing companion animals is a drastic food intake reduction. However, none of the diets currently available have proven satisfactory to many people or pets for reasons including increased stool volumes, reduced palatability, poor hair coats as a result of the diets' low fat content, but primarily because the diets do not sufficiently decrease the animals' hunger. When this occurs, the companion pets often scavenge and/or beg for food because of the sensation of constant hunger. As a result, the animal finds additional food, or pet owners feed the animal to stop the begging with the result being that no weight reduction occurs.

In short, it can be seen that for companion pets successful weight reduction involves not only decreased food intake, but as well an interdisciplinary, psychological treatment that involves the interrelationship between the companion animal and its human owner. This complex psychological interdependency makes weight reduction in companion pets even more difficult than it otherwise might be. In short, success at pet weight reduction involves initially convincing the owner that weight reduction is needed; secondly, the animal's food intake must be decreased for a sustained and regular period of time sufficient for weight reduction to occur; and third, the animal must be inhibited from constant scavenging and/or begging which tempts the owner to give in and increase the food intake to stop the begging.

In the past, certain drugs have been used in the treatment of obesity in mammals, including companion pets. These include drugs which decrease appetite such as amphetamines, drugs which cause nausea, decrease intestinal absorption, or increase metabolic rate such as thyroid hormones, and finally, drugs which either tranquilize or act as diuretics. None of the above have been generally effective. They often cause side effects, and tests of most have shown that such drugs are not only expensive, but ineffective in that when free choice fed with food, the animals often tend to avoid the food that contains the drug.

It therefore can be seen that there is a real and continuing need for a treatment for mammals, and especially companion pets, which is safe, efficacious, and which can successfully result in obesity reduction without changing the animal's behavioral patterns to such an extent that its relationship with its owner is changed. There is a further need for a treatment that sufficiently inhibits hunger or induces satiety in the animals.

This invention has, as its primary objective, the fulfillment of these needs.

SUMMARY OF THE INVENTION

A pet food composition containing a small but effective amount of simmondsin component to provide a simmondsin activity within the range of 0.1% by weight of said pet food mix dry matter to about 1.5% by weight of said pet food mix dry matter is described. Another part of the invention is a method of weight reduction and obesity prevention of companion pets by adding pet food that contains the above-defined range of simmondsin activity, contributed by a simmondsin component, simmondsin analogues or mixtures thereof such as that synthesized or derived from jojoba seeds, jojoba seed meal, defatted jojoba seed meal, or other jojoba sources, and thereafter feeding the pet food to a companion pet on a regular and sustained basis until sufficient weight reduction occurs, and obesity occurrence or recurrence is prevented. With respect to dogs, the pet food should contain at least 0.67% pure simmondsin by weight of said dog food mix dry matter. For cats, the pet food should contain at least 0.24% pure simmondsin by weight of said cat food mix dry matter.

Still another part of the invention is a method of weight maintenance in companion pets by adding the same simmondsin containing compounds to pet food in a concentration of at least 0.37% pure simmondsin by weight of said pet food mix dry matter of dogs, and at least 0.18% by weight for cats.

DETAILED DESCRIPTION OF THE INVENTION

Jojoba (Simmondsia chinensis or Californica) is a desert shrub native to southwestern United States and northwestern Mexico. It is commercially grown largely due to its low water requirements and to unique qualities of its oil, which has characteristics similar to sperm whale oil. Jojoba oil has many industrial uses and is widely used as an additive in mineral oils, cosmetics, pharmaceuticals, and numerous other products.

Defatted jojoba seed meal contains approximately 30% proteins, and its supplementation in animal feed has been reported as associated with food intake reduction and growth retardation (Booth, A. N., Elliger, C. A. and Wain, A. C., Jr., 1974. Isolation of a toxic factor from jojoba meal. Life Sci., 15: 1115–1120; Cokelaere, M. M. Buyse, J., Daenens, P., Decuypere, E., Kuhn, E. R. and Van Boven, M., 1993. Influence of jojoba seed meal supplementation on growth and organ function in rats. J. Agric. Food Chem., 41: 1444–1448). These articles indicate that jojoba seed meal contains simmondsins and suggest that it may work to induce food intake reduction by a toxic mechanics, see particularly Booth et al., 1974. cokelaere, et al., 1993 Journal of Agricultural Food Chemistry article, reports on the influence of jojoba seed meal supplementation on growth and organ function in rats. Other articles by Cokelaere, et al. report on the influence of pure simmondsin on food intake of rats and the effect on the fertility in rats after long-term jojoba seed meal supplementation. See Cokelaere, Influence of Pure Simmondsin on Food Intake in Rats, Journal of Agricultural Food Chemistry, 1992, 40; and Journal of Agricultural Food Chemistry, 1993, 41, 1449–1451, Fertility in Rats After Long-Term Jojoba Meal Supplementation.

None of these articles suggest the use of jojoba seed meal or its simmondsin analogues in a sustained and regular weight reduction program for companion pets. It is understandable that the Cokelaere articles did not make such a suggestion since transfer of data from rat experiments to higher animals is not at all a certainty and, as well, there is a fundamental difference between successful weight reduction for companion pets and the mere observation that an active or potential active may cause food consumption reduction in some manner. For example, as illustrated in the tests involving dogs hereinafter disclosed, food consumption reduction at levels within the range of 20% to 27% allows no weight reduction. Thus, for companion pets such as dogs, who are known to like a high calorie diet, a successful weight reduction program must involve food reduction at levels equal to or greater than 27%.

It has now surprisingly been discovered that, for reasons not yet completely understood, compounds that have simmondsin activity, and in particular defatted jojoba seed metal, when added to companion pet foods to achieve later defined levels of simmondsin activity, will successfully result in companion pet, and particularly dog and cat, weight reduction. This is done without causing the animal to be hungry and without significantly changing the animal's behavior patterns, and importantly without changing the animal's psychological interrelationship with the pet owner. As a result, the companion pet avoids the frequent begging and/or food scavenging that destroys diet efforts and the animal will, without any significant side effects or behavior pattern changes. Instead, the animals voluntarily practice eating habits that result in weight reduction.

In accordance with this invention, a companion pet is treated with a sufficient amount of a simmondsin component to provide from about 0.1% by weight of its daily dietary food dry matter mix to about 1.5% by weight of its daily dietary food dry matter mix of simmondsin activity. As used herein, simmondsin activity refers to a simmondsin-containing component that is present at a sufficient level to provide from about 0.1% by weight of the total dietary daily pet food mix dry matter to about 1.5% by weight of the daily dietary dog food mix dry matter of pure simmondsin. For weight maintenance, the preferred range from about 0.37–0.67% by weight of the simmondsin component for dogs, and from about 0.18–0.24% by weight of the simmondsin component for cats. The preferred range for weight loss is from about 0.67–1.0% by weight of the simmondsin component for dogs, and from about 0.24–1.0% by weight of the simmondsin component for cats.

The simmondsin activity can be derived from jojoba seeds, jojoba seed meal, defatted jojoba seed meal, and from other various jojoba sources. The simmondsin activity can also be derived from the pure compound simmondsin, from simmondsin-2'-ferulate, or from related cyanomethylene glycosides. Preferably, the simmondsin component is from defatted jojoba seed meal.

Presently, defatted jojoba seed meal is readily available, with it being a by-product of oil extraction process of the seeds of the jojoba plant. It is now normally discarded.

The method of administration or treatment with the simmondsin component can be by simply admixture (on a weight basis sufficient to provide the desired simmondsin activity) with conventional pet foods.

As those skilled in the art known, dry pet foods, typically dry dog foods, normally contain protein, fat, fiber, non-fiber carbohydrates, minerals, vitamins and moisture components. For example, as major ingredients there are typically one or two cereal grains, generally corn, wheat and/or rice. In addition, for a protein source they may contain poultry meal, by-product meat, meat and bone meal, or other animal or fish meal by-products. At times as well, grain protein supplements such as corn gluten, soybean meal or other oil seed meals may be added. Typical nutrient content in the food dry matter will be as follows. Crude protein from 14% to 50%, usually 20% to 25%. Crude fat from 5% to 25%, with current obesity management (usually containing lower fat levels such as at 5% to 8% and with super premium brands usually containing from 14% to 20% fat). Crude fiber usually is present in the range of from about 3% to 14%, usually about 5% to 7%, with the total mineral or ash content being within the range of 3% to 10%, usually 4% to 7%. The important point is not the precise formulation of the pet food, since many conventional and satisfactory ones for use in conjunction with the present invention are available on the market. Rather, the key to success is that a sufficient amount of simmondsin component be added to pet food rations, whichever formulation is used, to provide the simmondsin activity level at the range previously expressed.

The method of treating or administration is usually simple addition to the food prior to its extrusion or canning sufficient to provide the earlier-expressed simmondsin activity range, followed by free choice feeding of that food to the animal. However, it is conceivable that pure simmondsin, simmondsin-2'-ferulate or other cyanomethylene glycosides could be administered by injection or in tablet or powder form. However, it is currently believed that the most effective method is simple addition to normal food ration, since the result is to achieve a sufficient reduction in food intake to result in weight reduction and the prevention of obesity.

While tests have not yet been conducted on other companion pets or on other domestic livestock animals, it is conceivable and within the scope of the expected uses of the present invention that simmondsin components herein mentioned could be used successfully with other species. In fact, it is likely, although tests have not been conducted yet, that simmondsin and/or its analogues and/or its derivatives can be used as a means for successful weight reduction and obesity prevention for humans.

The following examples are offered to further illustrate, but not limit the invention.

EXAMPLES

Example 1

The examples set forth below show the effects of defatted jojoba seed meal in dog food for use in weight maintenance and weight reduction to achieve obesity correction and prevention. In these tests a high-calorie, highly-palatable, low-fiber dry dog food as currently available on the market was used. The diet was typical of a super premium dry dog food and had the following guaranteed analysis; crude protein 24–26%; crude fat 16–18%; crude fiber 3–4.5%; ash 5–6.5%; and moisture 7–9%. Defatted jojoba seed meal at a 4.5% weight level (0.37% simmondsin activity) and at an 8% weight level (0.67% simmondsin activity) was added to the diets. Simmondsin activity in the jojoba seed meal used was calculated as its percent simmondsin plus its percent simmondsin-2'-ferulate (SF2) times S2F's simmondsin content of 68%. The jojoba seed meal also contained 4.6% didemethyl simmondsin and 1.87% dimethyl simmondsin. When 10 dogs were allowed to choose either the leading selling dry dog food or one of the diets containing defatted jojoba seed meal, all 10 dogs preferred the jojoba-containing diet (over 85% of the total amount eaten by each dog was one of the jojoba-containing diets). They consumed 31.1 times more of the 4.5% jojoba diet than they did of the leading selling dry dog food, 74.6 times more of the 8% jojoba diet than they did of the leading selling dry dog food, and 70.1 times more of the 8% jojoba diet than they did of the leading selling dry canine weight reduction diet (over 88% of the total amount eaten by each dog was the 8% jojoba diet). As evidenced from the testing shown below, simmondsin activity level of 0.37% provided by defatted jojoba seed meal added at a weight level of 4.5% of the dry dog food results in a sufficient voluntary reduction in food intake to result in maintenance of body weight by dogs that were previously known to be obese dogs and natural overeaters. The addition of defatted jojoba seed meal at the 8% by weight level which provides a simmondsin activity of 0.67% resulted in a sufficient voluntary reduction in food intake by most obese dogs to result in a 2% to 3% per week decrease in body weight. This is the rate of weight reduction most commonly recommended for obese dogs so that the pet owner notices the weight decrease, but it occurs without risk of causing any health problems in the animal. In addition, the data show that the animals do not reject the diet, but eat it regularly, seem to like it, and will continue eating it on a regular and sustained basis such as required for the desired weight reduction. Finally, no adverse effects to date in the tests have been noticed.

The dogs selected for use in this study were known to be overeaters if a palatable diet was available. They were selected for use in this study because they were specifically the type in which obesity is a problem. The dogs are identified in the following table:

TABLE 1

DOGS, DIET AND METHOD USED

| | | Initial Body Weight | | Optimum | | |
|---|---|---|---|---|---|---|
| Dog # | Breed Type | Lbs. | % >Opt | Wt - Lbs | Sex | Age |
| 11 | Beagle | 25.2 | 19.9 | 21.0 | F | 8 |
| 19 | Fox Terrier | 25.1 | 0 | 25.1 | F | 9 |
| 30 | Pug | 21.6 | 19.8 | 18.0 | M | 5 |
| 31 | Pug | 17.6 | 17.4 | 15.0 | M | 4 |
| 40 | English Springer Spaniel | 50.3 | 35.8 | 37.0 | F-S | 10 |
| 43 | Labrador Retriever | 80.5 | 23.8 | 65.0 | M | 8 |
| 45 | Labrador Retriever | 79.5 | 20.5 | 66.0 | F | 8 |
| 53 | Boxer | 58.7 | 2.7 | 55.0 | F | 7 |
| 54 | Labrador Retriever | 68.2 | 24.1 | 55.0 | F | 8 |
| 55 | Labrador Retriever | 76.3 | 33.8 | 57.0 | M | 8 |
| W5 | Vizsla Cross | 115.5 | 28.4 | 90.0 | M-N | 6 |
| W6 | Labrador Retriever | 62.7 | (−10.3) | 70.0 | M | 5 |
| Avg: | | 55.5 | 16.4 | 47.8 | | 7.2 |

Five diets of identical composition, except for varying amounts of defatted jojoba seed meal replacing wheat germ meal, were prepared at the same time, from the same batch of ingredients. All were similar in nutrient content, exceeding the dogs' requirements for all nutrients. The diets were all high in fat and caloric density, and low in fiber, which is the opposite in all aspects to currently-available obesity correction and prevention diets. These diets were used because the high fat content makes them especially palatable for the animal. All dogs always had water available, were allowed free access to their diet from 10:00 a.m. to 6:00 p.m. daily and were weighed at 9:00 a.m. once weekly. Food intake was measured daily. Each dog was given a thorough physical exam by a veterinarian before the study, after six weeks, and another at the end of the study.

Table 2 shows controlled dogs using Diet A, which contained no jojoba meal and simply was a diet without any added simmondsin activity.

TABLE 2

DIET A = NO JOJOBA MEAL

| Dog | g eaten/kg B. wt/day. | | | |
|---|---|---|---|---|
| No. | Wk 1 | Wk 2 | Wk 3 | Wk 4 |
| 19 | 33.2 | 30.8 | 22.8 | 23.1 |
| 53 | 46.0 | 29.1 | 26.1 | 25.5 |
| W6 | 51.4 | 32.5 | 32.2 | 29.8 |
| Avg. | 43.5 | 30.8 | 27.0 | 26.1 |

% change-21.3% −6.0%
28 g/kg/day eaten (excluding first week)

| Dog | % Body Weight Change | | | | | % Above Opt Wt | |
|---|---|---|---|---|---|---|---|
| No. | Wk 1 | Wk 2 | Wk 3 | Wk 4 | Total | Initial | Final |
| 19 | +3.1 | +5.9 | (−1.8) | +1.6 | +8.9 | 0 | +8.9 |
| 53 | +11.5 | +2.4 | +0.4 | +0.2 | +14.9 | +2.7 | +18.0 |

TABLE 2-continued

| DIET A = NO JOJOBA MEAL | | | | | | | |
|---|---|---|---|---|---|---|---|
| W6 | +10.5 | +5.8 | +4.4 | +5.5 | +29.1 | (−10.3) | +24.4 |
| Avg. | +8.5 | +4.7 | +1.0 | +2.4 | +17.6 | | |

| | average + 2.7%/week excluding first week | | | |
|---|---|---|---|---|
| Dog | g/kg/ day | % B. wt change | % Above Optimum Body weight on A | |
| No. | Wk 1 | Wk 1 | Initial | Final |
| 45 | 36.6 | +6.0 | 13.6 | 20.5 |
| W5 | 28.5 | +10.5 | 16.1 | 28.3 |
| Avg. | 32.6 | +8.3 | 14.85 | 24.4 |

Table 2 demonstrates that the diet by itself, without any added simmondsin activity, was palatable, and that even after becoming accustomed to having it available, all the dogs on this control diet continued to consume excess amounts and become obese.

TABLE 3

| DIET D = 4.5% JOJOBA MEAL (0.37% SIMMONDSIN ACTIVITY) | | | |
|---|---|---|---|
| | g eaten/kg B. wt/day | | |
| Dog No. | Wk 1 | Wk 2 | Wk 3 |
| 11 | 20.0 | 19.9 | 18.7 |
| 30 | 20.4 | 16.4 | 19.1 |
| 31 | 34.7 | 22.2 | 18.9 |
| 40 | 23.8 | 16.5 | 17.3 |
| 43 | 23.4 | 18.8 | 22.1 |
| 54 | 25.6 | 22.9 | 24.1 |
| 55 | 24.4 | 23.4 | 24.5 |
| 45 | 19.4 | 21.2 | — |
| W5 | 16.4 | 17.4 | — |
| Avg. | 23.1 | 19.8 | 20.7 |

As shown, excluding the first week, dogs voluntarily reduced their food intake from 28 to 20.25 g/kg body weight/day, a 27.6% reduction, when 4.5% jojoba seed meal by weight to provide 0.37% simmondsin activity was added to the food.

TABLE 4

| Diet D = 4.5% Jojoba Meal (0.3 to 0.4% Simmondsin Activity) | | | | | | | | |
|---|---|---|---|---|---|---|---|---|
| Dog | % Body Weight Change | | | | | | % Above Opt Wt | |
| No. | Wk 1 | Wk 2 | Wk 3 | Wk 4 | Total | /wk | Initial | Final |
| 11 | −3.1 | −0.6 | +0.8 | — | −2.9 | −1.0 | 19.9 | 15.8 |
| 30 | −1.0 | −1.3 | −2.0 | +0.7 | −3.6 | −0.9 | 19.8 | 15.5 |

TABLE 4-continued

| Diet D = 4.5% Jojoba Meal (0.3 to 0.4% Simmondsin Activity) | | | | | | | | |
|---|---|---|---|---|---|---|---|---|
| Dog | % Body Weight Change | | | | | | % Above Opt Wt | |
| No. | Wk 1 | Wk 2 | Wk 3 | Wk 4 | Total | /wk | Initial | Final |
| 31 | +2.1 | −3.2 | −0.4 | — | −1.5 | −0.5 | 17.4 | 15.6 |
| 40 | −0.5 | +0.5 | −0.5 | — | −0.5 | −0.2 | 35.8 | 35.1 |
| 43 | +1.3 | −1.5 | +2.4 | — | +2.1 | +0.7 | 23.6 | 26.5 |
| 54 | +2.2 | +2.2 | −0.5 | — | +3.9 | +1.3 | 24.1 | 28.9 |
| 55 | +5.3 | −2.2 | +1.3 | — | +4.3 | +1.4 | 33.8 | 39.5 |
| 45 | 0.0 | −0.3 | — | — | −0.3 | −0.2 | 20.5 | 20.1 |
| W5 | −1.5 | +0.2 | — | — | −1.3 | −0.7 | 28.3 | 26.6 |
| Avg. | +0.5 | −0.7 | +0.16 | | +0.7 | +0.2 | 24.8 | 24.8 |

All the dogs using this diet, which differed from the Table 2 diet simply by the addition of 4.5% jojoba seed meal, maintained the dog's body weight even when they were allowed free access to this high energy, highly palatable diet containing 0.37% simmondsin activity. In contrast to dogs receiving the same diet without simmondsin activity, they did not continue to gain weight as the detailed evidence shows. It is worthy of note that these animals maintained weight even though they voluntarily decreased their food intake by an average of 27.6%.

In the study shown in Table 5 the same diet was used, except that the amount of simmondsin activity was increased to 0.67% by increasing the amount of the defined jojoba seed meal to 8% of the diet by weight.

TABLE 5

| Diet E = 8.0% Jojoba Meal (0.67% Simmondsin Activity | | | | | |
|---|---|---|---|---|---|
| Dog | g/kg body weight/day eaten | | | | |
| No. | Wk 1 | Wk 2 | Wk 3 | Wk 4 | Wk 5 |
| 11 | 15.5 | 15.2 | 15.5 | 14.5 | 15.6 |
| 30 | 14.0 | 10.1 | 15.1 | 7.4 | |
| 31 | 17.4 | 17.5 | 23.4 | 17.8 | 19.2 |
| 40 | 12.4 | 12.8 | 12.2 | 11.8 | 10.9 |
| 43 | 16.3 | 19.2 | 15.9 | 17.8 | 20.0 |
| 54 | 17.6 | 14.7 | 16.7 | 12.2 | 18.7 |
| 55 | 25.9 | 19.8 | 18.9 | 19.9 | 17.3 |
| 45 | 16.5 | 14.7 | 15.0 | 18.3 | 18.2 |
| W5 | 14.7 | 13.2 | 14.1 | 13.5 | 10.8 |
| 53 | 20.7 | 20.9 | 18.5 | 19.1 | |
| W6 | 15.2 | 16.5 | 16.9 | 15.4 | |
| Avg. B. Wt./day eaten | 16.9 | 15.9 | 16.6 | 16.0 | 16.3 = 16.34 g/kg |

As shown, dogs voluntarily reduced their food intake from 28 to 16.34 g/kg body wt./day, a 41.6% reducton, when 8% jojoba seed meal by weight providing 0.67% simmondsin activity was added to the food.

TABLE 6

| Diet E = 8.0% Jojoba Meal (0.5 to 0.7% Simmondsin Activity) | | | | | | | | | |
|---|---|---|---|---|---|---|---|---|---|
| | % Body Weight Change | | | | | | | % Above or Below Opt. Wt. | |
| Dog No. | Wk. 1 | Wk. 2 | Wk. 3 | Wk. 4 | Wk. 5 | Total | /Wk | Initial | Final |
| 11 | −5.0 | −2.7 | −0.8 | −1.0 | −3.4 | −12.2 | −2.4 | +15.8 | +2.2 |
| 30 | −2.3 | −4.4 | −0.2 | −7.2 | | −15.2 | −3.8 | +15.2 | 0.0 |
| 31 | −4.5 | −2.9 | −5.9 | −1.6 | −5.4 | −19.5 | −3.9 | +15.6 | (−6.9) |

TABLE 6-continued

Diet E = 8.0% Jojoba Meal (0.5 to 0.7% Simmondsin Activity)

| | % Body Weight Change | | | | | | | % Above or Below Opt. Wt. | |
|---|---|---|---|---|---|---|---|---|---|
| Dog No. | Wk. 1 | Wk. 2 | Wk. 3 | Wk. 4 | Wk. 5 | Total | /Wk | Initial | Final |
| 40 | −4.0 | −1.9 | −1.2 | −5.4 | +0.7 | −11.4 | −2.3 | +35.2 | +19.7 |
| 43 | −1.5 | +0.5 | +1.1 | −2.1 | +1.3 | +0.6 | +0.1 | +24.4 | +25.4 |
| 54 | −0.6 | −2.8 | −1.5 | −2.4 | +1.7 | −5.5 | −1.1 | +28.9 | +21.8 |
| 55 | +3.5 | −2.0 | −0.8 | +0.9 | −2.5 | −0.9 | −0.2 | +39.5 | +38.2 |
| 45 | −0.9 | −1.2 | +0.5 | −3.8 | +1.3 | −4.1 | −0.8 | +20.1 | +15.2 |
| W5 | +0.5 | −1.7 | −1.9 | −0.5 | −1.4 | −4.8 | −1.0 | +26.7 | +20.6 |
| 53 | −5.6 | −5.8 | −3.5 | −7.6 | | −20.6 | −5.2 | +18.0 | (−6.4) |
| W6 | −6.4 | −2.7 | −1.7 | −2.1 | | −12.4 | −3.1 | +15.8 | +1.6 |
| Avg. | −2.44 | −2.51 | −1.45 | −2.98 | −0.96 | −9.7 | −2.2 | +23.2 | +11.9 |

As can be seen, most obese dogs using the 0.67% simmondsin activity food on a free choice basis voluntarily reduce their food intake sufficiently when fed this diet to lose weight at the widely recommended rate of 2% to 3% per week. Moreover, the animals exhibited no changes in behavior and no adverse health effects during the tests.

Example 2

The examples set forth below show the effects of defatted jojoba seed meal in cat food for use in weight maintenance and weight reduction to achieve obesity correction and prevention.

Diet Preparation and Content

Six dry chicken by-product meal-based diets were extruded on a Wenger X-25, coated, sealed in 8 lb-4 ply Fresco gas impermeable bags containing a one-way valve, and labeled FC-0, FC-1, FC-2, FC-3, FC-4 and FC-5 at CJ Foods, Inc., Pawnee City, Nebr., on Jan. 21, 1998. The dry mix for extrusion had been prepared the previous week by Lortschers Agri Services, Inc., Bern., Kans. Diet pellets were 6.5–7 mm D×5.5–6 mm L and the diet's densities were 25–28.5 lbs/cu ft uncoated and 29 to 30 lbs/cu ft coated.

As shown in Table 7, the only difference in the diets was 0, 2, 4, 8, 12 or 16% jojoba seed meal in diets FC-0, 1, 2, 3, 4 and 5, respectively, with the jojoba replacing the Diet FC-0, either 1, 2, 3, 4 or 6% corn gluten meal and 0.5, 1, 2.5, 4 or 5% rice and oat groats. The content of all nutrients in the diets were nearly identical and exceeded AAFCO requirements for cats for growth and reproduction as shown in Tables 8 and 9. The diets contained less than detection limits of aflatoxin and vomitoxin, and there was little oxidation or rancidity present as indicated by a peroxide value of 6.2 meq/kg of fat in unpackaged diet 2 weeks following is production (Table 9).

Simmondsin activity was determined in the jojoba seed meal used and from this, and the amount of jojoba in the diet, the simmondsin activity in each diet calculated. This value was compared to that determination by analysis of each diet. Although, as shown in Table 10, these amounts were similar, simmondsin activity in each diet calculated from the amount of jojoba seed meal in that diet appears to be more accurate.

Diet Palatability

Diet palatability was determined by offering excess amounts of the two diets being tested to 10 cats for 2 consecutive days feeding. These cats were different from those used to determine the diets' effects on food intake and body weight, and were cats which had not previously had access to these diets and were not routinely fed the commercial diet they were tested against. A cat was considered to prefer one diet to the other if it ate over twice as much of that diet as it did of the other diet offered.

Jojoba seed meal, at least up to 8% in the diet replacing corn gluten meal, rice and oat groats (Table 7), had no effect on diet palatability. There was 0 difference in preference between Diet FC-0 containing no jojoba seed meal and FC-3 containing 8%, although FC-3 was slightly preferred with a ratio of the percent that each diet contributed to the total amount consumed being 1.1 FC-3 to 1.0 FC-0. Two cats preferred FC-3, 2 FC-0 and for 6 there was no difference in preference.

Diet FC-3 (8% jojoba diet) was preferred to the leading selling dry cat food (Purina Cat Chow) by a ratio of 2.3 to 1, i.e., 10 cats in 2 daily feedings consumed an average of 70% diet FC-3 and 30% Cat Chow for a ratio of 70% to 30% or 2.3 times more of diet FC-3 than Cat Chow consumed. Seven cats preferred FC-3, 2 Cat Chow and 1 there was no difference in preference.

These studies demonstrate that the diets used in this study are quite palatable for most cats. As a result, any effects that jojoba seed meal in these diets may have on the amount of food consumed is unlikely to be due to its effect on the diet's palatability.

Feeding Study Methods

All feeding studies were conducted from Feb. 26, 1998 to Sep. 17, 1998 at Summit Ridge Farms, Susquehanna, Pa. All were adult domestic short-haired cats. Most were quite old, as they had been in the colony 3 to 14 years and were thought to have been 1 to 4 years of age when they were obtained (Table 11).

Just before beginning the study, all cats were given a thorough physical examination by a veterinarian. No abnormalities or diseases were noted in any of the cats used. Each cat's current and estimated optimum weight were determined during this exam. As shown in Table 11, the cats initially ranged from 11 to 37.5% above their estimated optimum weight, and all were 14% or more overweight when they were first fed a jojoba-containing diet.

All cats were housed individually with 12 hr light and dark cycles, and at a temperature of 60 to 85° F. and humidity of 30 to 70%. Food bowls, water bowls and litter boxes were emptied and sanitized daily. Water and the diet being fed were always available for free choice consumption except the night before the cats were to be weighed, when food bowls were removed. The amount of diet consumed was recorded, diet uneaten discarded and fresh diet fed daily. Weekly, following an overnight (14-hr) fast, each cat was weighed.

Each cat was initially fed the non-jojoba containing diet FC-0 for 4 weeks, or until it was 14% or more over its estimated optimum weight, at which time it was fed either the diet containing 4% (FC-2) or 8% (FC-3) jojoba. Cats whose weight decreased by more than 4.6% in 1 week, or 6% in 2 weeks, were changed to the next lower jojoba-containing diet. Whereas cats whose weight did not decrease by greater than 1.6% and 2 weeks were changed to the next higher jojoba-containing diet.

When a cat was within 2.0% of its optimum weight, it was changed to a lower jojoba-containing diet; either that containing 2% or 4% (FC-1 or FC-2). If optimum body weight wasn't maintained when this diet was fed, the cat was changed to a higher jojoba-containing diet if it had gained weight and a lower jojoba-containing diet if it had lost weight. When the cat's weight had been maintained within 4% of its optimum for 4 weeks while eating the same diet, it was given a thorough physical exam by a veterinarian and removed from the study. No abnormalities or disease were noted in any of he cats completing the study.

Feeding Study Results

As shown in Table 11, 11 of 12 cats maintained excess body weight (±3.0% change) or became more overweight (4.3 to 8.2% gain) when fed the non-jojoba-containing diet FC-0 for 4 to 10 weeks (5.9±2.2 mean±SD). One cat, #35, failed to maintain excess body weight when fed the non-jojoba containing diet, so was not fed a jojoba-containing diet and was removed from the study. This cat's consumption of this diet was slightly but not significantly less than that consumed by the other cats (12.2±2.1 vs 14.6±4.1 g/kg body wt/d), and was nearly 30% more than that consumed by cats number 47 and 09 who maintained their weight (Table 12).

The average amount of each diet consumed by each cat is shown in Table 12. With the exception of cats that were not overweight when a diet was fed, each increase in jojoba in the diet resulted in a greater decrease in food intake (Table 13). This appeared to occur in a hyperbolic, not straight line, manner as has been shown in other species, i.e., an increase in simmondsin activity from 0.12 to 0.24% resulted in a 13% additional decrease in food intake (from a 17.8 to 30.7% decrease), whereas twice this amount of increase in simmondsin activity (from 0.24 to 0.49%) was necessary to result in an additional 15% decrease (from a 30.7 to 45.9% decrease).

Simmondsin activity's effect on food intake did not appear to differ in most cats regardless of their body weight. As shown in Table 14, the amount per kg of body weight consumed did not appear the differ whether the cat was overweight or was at its optimum weight when the same diet was fed. The difference in this amount averaged only 0.4±10.2% in the 5 cats that received the same diet both before and after reduction to their optimum weight (Table 14).

In 3 cats (#46, 47 and K8) 2% jojoba in the diet (FC-1) was not sufficient to decrease their food intake, although higher amounts did (Table 14). Even cats whose intake of the 2% jojoba diet (FC-1) were decreased, this decrease was not sufficient to result in a decrease in body weight (Table 15). The exception to this was 1 cat (Jr) whose intake of the 2% jojoba diet (FC-1) was reduced substantially more than the others (39% vs 17 to 25.5%) and as a result, its body weight decreased an average of 0.5%/week during the 6 weeks this diet was fed. Four percent jojoba in the diet (FC-2) was sufficient to decrease all cats food intake enough (18.1 to 36.7%) to induce weight loss although the amount of loss varied between individual cats from an average of 0.1%/week to 5.0%/week. Further increases in jojoba in the diet resulted in greater reductions in food intake, which usually but not always caused a more rapid weight loss (Table 15).

The degree of obesity, average weekly change in body weight, duration and order that each diet was fed to each cat are shown in Table 16. The mean, sample standard deviation and range of each of these values for each diet are given in Table 17. The number of cats that responded similarly and differently when fed each diet is also described in Table 17.

Cat H02 became ill after reducing from being 15.4% to 1.2% overweight when fed the 4% jojoba diet (FC-2) for 2 weeks and the 8% jojoba diet (FC-3) for 5 weeks, with an average weight loss of 1.85%±1.5%/week. This cat's white blood cell count and blood glucose were both slightly elevated (Table 18). Following unsuccessful therapy this at least 14-year-old cat was euthanized, necropsied and found to have hypertrophic cardiomyopathy (NY State College of Veterinary Medicine, Surgical Pathology Services, Jun. 24, 1998 report). Mild periacinar atrophy of the hepatocytes but no lipidosis was evident. The kidneys showed mild acute tubular necrosis with regeneration and mild linear interstitial fribrosis with occasional sclerotic glomeruli. Besides the cardiac and lung changes indicative of left heart failure, no other significant lessons were found.

Cat 09 developed an upper respiratory disease after reducting from being 37% and 8% overweight when fed the 8% jojoba diet (FC-3) for 2 weeks then the 4% jojoba diet (FC-2) for 8 weeks, with an average loss 2.3%±2.0%/week. Although this cat was successfully treated, its body weight fell to 1.4% below its optimum during therapy, so it was not returned to the study.

Cat K8 also developed an upper respiratory disease, but following treatment and recovery was still 3.6% overweight so was returned to the study. No other disease problems or abnormalities were observed in any of the other cats.

Complete bond counts and serum chemistries were obtained in 7 of the cats at various times during the study (Table 18). All values were normal for all cats except for the slight glucose and leukocyte elevations in cat H02 that died of cardiomyopathy as described above, and a mild anemia in cat #48 (Table 18). This cat's erythrocytes, hemoglobin concentration and lymphocytes were just below normal ($4.87\times10^6$ RBC's/cu mm and 8.2% hemoglobin vs colony normals of 5.1 or greater RBC's and 8.9% hemoglobin) after having consumed jojoba containing diets for 24 weeks (Table 16), at which time its T-4 was normal, liver and kidney function tests were normal, and it was negative for giardia and feline leukemia. Its RBC's hemoglobin concentration and hematocrit were all decreased further one week after being changed to a commercial diet (Dry Science Diet Feline Maintenance, Hills) (Table 18), but its RBC production had increased from 43,000 to 286,000, and lymphocytes had increased from 670 to 970/cu mm. One week later all values had increased further toward normal, although RBC production had slowed to 181,000.

Discussion and Conclusions

Laboratory Study

As this study demonstrates, as occurs in several other species of animals, jojoba seed meal in the cat's diet results in a voluntary decrease in food intake in a dose-dependent hyperbolic manner without affecting the diet's palatability. A comparison of these effects in cats and dogs are shown in Table 19.

The same amount of jojoba seed meal and simmondsin activity in the dogs' diet and in the cats' diet results in a similar decrease in their food intake, and a sufficiently high amount in the diet results in a similar decrease in their body weight (Table 19). However, in these studies, because the intake of all diets was so much lower for cats than it was for dogs, the cats gained less weight or lost more weight than did dogs fed diets with similar amounts of jojoba. Cats consumed only about one-half as much as dogs of each of the three diets containing 0, 4 to 4.5% or 8% jojoba seed meal (14.6 vs 28, 10 vs 21, and 7.2 vs 16.6 g of food/kg/d for cats vs dogs fed each of the 3 diets respectively). This may have occurred because the cats' diets were less palatable for them than were the dogs' diets for them. The 4.5% jojoba-containing canine diet was preferred by dogs to Purina Dog Chow 26 to 1, and was preferred by all 10 dogs fed, whereas the 4% jojoba-containing feline diet was preferred by cats to Purina Cat Chow by only 2.3 to 1, and was preferred by only 7 of 10 cats, 2 preferring Cat Chow and 1 with no preference between the two diets. These results suggest that the jojoba diets were less palatable for cats than were the jojoba diets for dogs resulting in the lower intake jojoba diets by the cats. However, just as likely, the dogs may simply have been greater overeaters than were the cats.

In this study the diets required for reduction of cats to their estimated optimum body weight for:

- 4 of 11 cats was the 4% jojoba diet (FC-2), which resulted in a weight loss of 1.4 to 3.5%/week,
- 6 of 11 cats was the 8% jojoba diet (FC-3), which resulted in a weight loss of 2.0 to 2.7%/week (one cat, H04, lost 5.4%/week when fed 8% jojoba, but maintained weight when fed 4% jojoba) (Table 16), and
- 1 of 11 cats was the 12% jojoba diet (FC-4), which resulted in a weight of 2.3%/week (a loss of only 0.4%/week occurred when 8% jojoba was fed to the cat #48) (Table 16).

Following reduction to optimum weight to maintain this weight appeared to require for:

- 3 of 9 cats the 2% jojoba diet,
- 2 of 9 cats the 4% jojoba diet, and for
- 4 of 9 cats the 3% jojoba diet because they gained weight when fed 2% jojoba but lost weight when fed 4% jojoba (+2.8 & −1.8, +0.5 & −2.1, +2.0 & −3.7, and +1.2 & −1.5% change/week when each cat was fed the 2% and the 4% jojoba diet, respectively, Table 16).

TABLE 7

Formulas for Diets Used for Jojoba Diet Laboratory Study

| | Percent in Diets | | | | | |
|---|---|---|---|---|---|---|
| Mix Ingredients | FC-0 | FC-1 | FC-2 | FC-3 | FC-4 | FC-5 |
| Jojoba Seed meal | 0 | 2 | 4 | 8 | 12 | 16 |
| Corn gluten meal | 11 | 10 | 9 | 8 | 7 | 5 |
| Rice, brewers | 25 | 24.5 | 24 | 22.5 | 21 | 20 |
| Oat groats | 25 | 24.5 | 24 | 22.5 | 21 | 20 |
| Chicken by-product meal | | | | 35 | | |
| Flaxseed oil | | | | 1.35 | | |
| Potassium citrate | | | | 1.25 | | |
| Vitamin premix (LasiPet) | | | | 0.500 | | |
| Choline chloride, 60% | | | | 0.275 | | |
| Salt iodized | | | | 0.275 | | |

TABLE 7-continued

Formulas for Diets Used for Jojoba Diet Laboratory Study

| | Percent in Diets | | | | | |
|---|---|---|---|---|---|---|
| Mix Ingredients | FC-0 | FC-1 | FC-2 | FC-3 | FC-4 | FC-5 |
| D1-methionine | | | | 0.275 | | |
| Taurine | | | | 0.045 | | |
| Zinc oxide | | | | 0.015 | | |
| Naturox plus (Kemin Inds) | | | | 0.015 | | |
| External Coatings | | | | | | |
| Poultry fat (containing Coviox antioxidant) | | | | 11.50 | | |
| DCPE dry powder palatant (AFB, Inc.) | | | | 1.50 | | |

TABLE 8

Nutrient Content in Diets Used for Fat Cat Diet Laboratory Study

| | FC-0 | FC-3 | | FC-5 | AAFCO Growth |
|---|---|---|---|---|---|
| Nutrient | Anal.[2] | Calc | Anal.[2] | Anal.[2] | Req. |
| Moisture - % | 10.2 | | 9.94 | 8.75 | at9.0 |
| Crude protein - % | 31.44 | 31.1 | 31.0 | 31.56 | 27.3 |
| Crude Fat - % | 19.41 | 18.4 | 18.42 | 18.30 | 8.2 |
| n-6 FA's - % | | 3.95 | | | 0.47 |
| n-3 FA's - % | | 0.93 | | | |
| n6:n3 | | 4.2:1 | | | |
| Calories-kcal ME/g | | 3.9 | 3.82 | | at3.64 |
| Crude Fiber - % | 0.27 | 2.2 | 1.04 | 0.97 | — |
| Ash[3] - % | 6.22 | 5.2 | 6.22 | 6.01 | — |
| Calcium[3] - % | 1.28 | 1.05 | 1.19 | 1.34 | 0.91 |
| Phosphorus[3] - % | 0.96 | 0.86 | 0.945 | 0.891 | 0.73 |
| Sodium - % | 0.26 | 0.24 | 0.255 | 0.193 | 0.18 |
| Potassium - % | 0.58 | 0.76 | 0.59 | 0.58 | 0.55 |
| Magnesium - % | 0.074 | 0.08 | 0.083 | 0.091 | 0.07 |
| Iron - ppm | 215 | 150 | 226 | 226 | 73 |
| Copper - ppm | 6.0 | 9.4 | 6.0 | 6.0 | 4.6 |
| Zinc - ppm | 148 | 163 | 125 | 121 | 68 |
| Manganese - ppm | 18 | 16.2 | 19 | 20 | 6.8 |
| Selenium - ppm | — | 0.49 | — | — | 0.09 |
| Sulfur - % | 0.47 | — | 0.45 | 0.44 | — |

[1]Calculated essential amino acid and vitamin content of diets are shown in Table 9.
[2]As determined and reported 02/05/98 by Midwest Laboratories, Inc., Omaha, Nebraska. Diet FC-3 was also found to contain less than the detection limit of 2 ppb aflatoxin and 0.5 ppm vomitoxin, and 2 weeks following production to have a peroxide value of 6.2 meg/kg fat.
[3]Analysis suggest regular ash poultry meal was used. Had low ash as requested been used, expected ash, calcium and phosphorus content would have been 1.0, 0.2 and 0.15% lower, respectively.

TABLE 9

Essential Amino Acid and Vitamin Content in Diet FC-3[1] as Compared to AAFCO Requirements for Growth, Reproduction and Maintenance

| | | Calculated in Diet | |
|---|---|---|---|
| Amino Acids | Required | % | % of Growth Reg. |
| Taurine | 0.09 | 0.145 added | 159+ |
| Arginine | 1.14[2] | 1.96 | 172 |
| Histidine | 0.28 | 0.78 | 279 |

TABLE 9-continued

Essential Amino Acid and Vitamin Content in Diet FC-3[1] as Compared to AAFCO Requirements for Growth, Reproduction and Maintenance

| | | | |
|---|---|---|---|
| Isoleucine | 0.47 | 1.16 | 247 |
| Leucine | 1.14 | 2.59 | 227 |
| Lysine | 1.09[2] | 1.35 | 124 |
| Meth + Cyst | 1.00 | 1.37 | 137 |
| Phenyl + Tyro | 0.80 | 2.18 | 273 |
| Threonine | 0.66 | 1.15 | 174 |
| Tryptophan | 0.23[2] | 0.31 | 135 |
| Valine | 0.66 | 1.33 | 238 |

| | | In Diet | |
|---|---|---|---|
| Vitamins | Required | Calculated | Added |
| A - 1000 IU/kg | 8.2[2] | — | 18 |
| D - 100 IU/kg | 6.8[2] | — | 18 |
| E - IU/kg | 27.3 | — | 185 |
| Thiamine - mg/kg | 4.6 | 8.4 | 3.5 |
| Riboflavin - mg/kg | 3.6 | 12.1 | 7.9 |
| Pantothenate - mg/kg | 4.6 | 7 | 3.5 |
| Nyacin - mg/kg | 55.0 | 74 | 41 |
| Pyridoxine - mg/kg | 3.6 | 4.5 | 36 |
| Folic Acid - mg/kg | 0.73 | 0.75 | 0.3 |
| Biotin - mg/kg | 0.063 | 0.17 | 0.035 |
| B-12 - mg/kg | 0.018 | — | 0.08 |
| Choline - mg/kg | 2184.0 | — | 1100 |

[1]All diets would contain a similar amount. See Table 8 for other nutrients content.

TABLE 9-continued

Essential Amino Acid and Vitamin Content in Diet FC-3[1] as Compared to AAFCO Requirements for Growth, Reproduction and Maintenance

[2]For maintenance 0.95% arginine, 0.76% lysine, 0.15% tryptophan, 4600 vitamin A and 460 vitamin D are required instead of the amounts shown.

TABLE 10

Jojoba Content and Simmondsin Activity in Diets Fed

| | Jojoba Seed | Calculated[2] Simmondsin Activity-% | | Analyzed[3] Simmondsin Activity-% | |
|---|---|---|---|---|---|
| Diet | Meal[1]-% | Total | Bioactive[4] | Total | Bioactive[4] |
| FC-0 | 0 | 0 | 0 | 0 | 0 |
| FC-1 | 2 | 0.22 | 0.12 | 0.14 | 0.09 |
| FC-2 | 4 | 0.44 | 0.24 | 0.50 | 0.28 |
| FC-3 | 8 | 0.69 | 0.49 | 0.80 | 0.43 |
| FC-4 | 12 | 1.33 | 0.73 | 1.02 | 0.57 |
| FC-5 | 16 | 1.78 | 0.98 | 1.31 | 0.73 |

[1]Obtained from Floratech, Gilbert, Arizona, 12/97.

[2]Calculated from the percent jojoba seed meal in the diet times its simmondsin activity of 11.11% total and 6.11% bioactive; as reported 04/02/98 by Dr. Tom Abbott, new Crops Research Lab, USDA, NCAUR, Peoria, IL.

[3]As assayed in that diet and reported 04/22/98 by the above laboratory.

[4]Bioactive simmondsin activity in the percent simmondsin plus 0.68 times the percent simmondsin ferrulate 1 and 2 activity, which by molecular weight are 68% simmondsin.

TABLE 11

Cats Evaluated and Their Degree of Obesity Just Before Feeding Jojoba Containing Diets

| | | | Est | Percent Overwt at End of | | Change in | No. of |
|---|---|---|---|---|---|---|---|
| Cat ID | Years[1] in Colony | Sex | Opt Wt-kg | First Week FC-0 Fed | Last Week FC-0 Fed | % Overweight | Weeks FC-0 Fed |
| 35 | 6 | MC | 4.0 | 13.3 | 4.0 | −9.3 | 10 |
| H04 | 10 | FS | 4.0 | 11.0 | 14.0 | +3.0 | 10 |
| 46 | 6 | MC | 5.0 | 17.0 | 14.0 | −3.0 | 10 |
| Jr | 14 | MC | 4.0 | 14.5 | 18.8 | +4.3 | 7 |
| H02 | 14 | MC | 5.0 | 9.8 | 15.4 | +5.6 | 6 |
| 47 | 6 | MC | 5.5 | 21.3 | 18.5 | −2.8 | 5 |
| K8 | 3 | MC | 4.5 | 36.0 | 33.8 | −2.2 | 5 |
| Mem | 13 | FS | 4.5 | 10.7 | 18.9 | +8.2 | 5 |
| 48 | 6 | MC | 5.0 | 14.6 | 20.4 | +5.8 | 5 |
| 55 | 5 | MC | 5.5 | 32.0 | 33.3 | +1.3 | 4 |
| 42 | 6 | F | 4.0 | 23.0 | 23.8 | +0.8 | 4 |
| 09 | 7 | MC | 5.5 | 37.5 | 36.7 | −0.8 | 4 |
| Avg[3] | 8.2 | 8 MC | 4.77 | 20.67 | 22.51 | +1.84 | 5.9 |
| ±SD | 3.89 | 2 FS 1 F | ±0.61 | ±10.26 | ±8.30 | ±3.84 | ±2.2 |

TABLE 11-continued

| Cats Evaluated and Their Degree of Obesity Just Before Feeding Jojoba Containing Diets | | | | | | | |
|---|---|---|---|---|---|---|---|
| | | | Est | Percent Overwt at End of | | Change in | No. of |
| Cat ID | Years[1] in Colony | Sex | Opt Wt-kg | First Week FC-0 Fed | Last Week FC-0 Fed | % Overweight | Weeks FC-0 Fed |

[1]Each cat is at least as old as shown and may be as much as 1 to 4 years older. Upon arrival into this colony, some were thought to have been up to 4 years old at that time.
[2]All cats except number 35 were fed jojoba containing diets following the last week that Diet FC-0 was fed.
[3]Excluding Cat 35, which was dropped from the study after being fed Diet FC-0 for 10 weeks because it did not maintain excess body weight on this non-jojoba containing diet.

TABLE 12

| Food Intake Affect of Jojoba Seed Meal In Feline Diets[1] | | | | | | | |
|---|---|---|---|---|---|---|---|
| | Grams/kg body wt eaten (Avg ± SD), Weeks Diet Fed and Percent Change from Diet FC-0 | | | | | | |
| CAT | Diet FC-0 | Wks | Diet FC-1 | Wks | % Chg | Diet FC-2 | Wks |
| 35 | 12.16 ± 2.10 | 10 | | | | | |
| H04 | 14.64 ± 5.52 | 10 | | | | 10.40[2] ± 4.97 | 4 |
| 46 | 12.73 ± 5.03 | 10 | 14.16[2] ± 6.18 | 4 | +11.2 | 6.65 ± 5.10 | 2 |
| Jr | 23.41 ± 7.54 | 7 | 14.20 ± 6.71 | 6 | −39.3 | 12.07 ± 7.95 | 3 |
| H02 | 19.67 ± 5.68 | 6 | | | | 16.12 ± 6.09 | 2 |
| 47 | 9.34 ± 1.56 | 5 | 11.30[2] ± 3.85 | 5 | +35.8 | 8.16 ± 3.14 | 10 |
| K8 | 15.61 ± 7.08 | 5 | 15.22 ± 7.12 | 2 | −2.5 | 11.07 ± 5.96 | 11 |
| Merri | 13.96 ± 3.42 | 5 | 11.39 ± 4.13 | 6 | −17.0 | 10.09 ± 3.51 | 2 |
| 48 | 14.41 ± 5.87 | 5 | 12.64 ± 5.11 | 2 | −12.3 | 10.03 ± 3.49 | 7 |
| 55 | 12.21 ± 1.96 | 4 | 9.75[2] ± 4.95 | 4 | −20.2 | 8.02 ± 3.32 | 3 |
| 42 | 15.30 ± 2.96 | 4 | 11.39[2] ± 4.68 | 4 | −25.5 | 11.49 ± 4.18 | 2 |
| 09 | 9.54 ± 1.56 | 4 | | | | 5.84 ± 2.28 | 8 |
| All[3] | 14.62 ± 4.10 | 5.9 ± 2.2 | 12.51 ± 1.84 | 4.13 ± 1.55 | −8.73 ± 23.4 | 10.00 ± 2.85 | 4.91 ± 3.45 |

| | Grams/kg body wt eaten (Avg ± SD), Weeks Diet Fed and Percent Change from Diet FC-0 | | | | | | |
|---|---|---|---|---|---|---|---|
| CAT | % Chg | Diet FC-3 | Wks | % Chg | Diet FC-4 | Wks | % Chg |
| 35 | | | | | | | |
| H04 | −29.0 | 7.74 ± 5.53 | 2 | −47.1 | | | |
| 46 | −47.7 | 6.18 ± 4.27 | 5 | −51.5 | | | |
| Jr | −48.4 | | | | | | |
| H02 | −18.1 | 8.22 ± 4.21 | 5 | −58.2 | | | |
| 47 | −12.6 | 7.85 ± 4.24 | 5 | −16.0 | | | |
| K8 | −29.1 | 7.75 ± 4.55 | 5 | −50.3 | | | |
| Merri | −27.7 | 6.74 ± 3.84 | 8 | −51.7 | | | |
| 48 | −25.2 | 9.08 ± 2.98 | 9 | −37.0 | 7.31 ± 3.09 | 6 | −49.2 |
| 55 | −34.3 | 5.20 ± 3.10 | 9 | −57.4 | | | |
| 42 | −24.9 | 7.56 ± 3.36 | 10 | −50.6 | | | |
| 09 | −38.7 | 5.82 ± 2.30 | 2 | −39.0 | | | |
| All[3] | −30.5 ± 11.15 | 7.21 ± 1.20 | 6.0 ± 2.87 | −45.9 ± 12.53 | 7.31 ± 3.09 | 6 | −49.2 |

[1]Diets FC-0, 1, 2, 3 and 4 Contain 0, 2, 4, 8 and 12% jojoba seed meal, respectively (Table 1) which provides the nutrient content and simmondsin activity described in Tables 2, 3 and 4.
[2]This intake occurred entirely when the cat was near its optimum weight, whereas intake of all other diets was when the cat was above this weight.
[3]Excluding cat #35.

TABLE 13

| Percent Decrease in Food Intake with Increased Simmondsin Activity in the Diets of Overweight Cats | | | | |
|---|---|---|---|---|
| | Bioactive Simmondsin Activity in Diet - % | | | |
| Cat | 0.12 | 0.24 | 0.49 | 0.73 |
| H04 | | | 47.1 | |
| 46 | | 47.7 | 51.5 | |

TABLE 13-continued

| Percent Decrease in Food Intake with Increased Simmondsin Activity in the Diets of Overweight Cats | | | | |
|---|---|---|---|---|
| | Bioactive Simmondsin Activity in Diet - % | | | |
| Cat | 0.12 | 0.24 | 0.49 | 0.73 |
| Jr | 39.3 | 48.4 | | |
| H02 | | 18.1 | 58.2 | |

TABLE 13-continued

Percent Decrease in Food Intake with Increased Simmondsin Activity in the Diets of Overweight Cats

| Cat | Bioactive Simmondsin Activity in Diet - % | | | |
|---|---|---|---|---|
| | 0.12 | 0.24 | 0.49 | 0.73 |
| 47 | | 12.6 | 16.0 | |
| K8 | 2.5 | 29.1 | 50.3 | |
| Merri | 17.0 | 27.7 | 51.8 | |
| 48 | 12.3 | 25.2 | 37.0 | 49.2 |
| 55 | | 34.3 | 57.4 | |
| 42 | | 24.9 | 50.6 | |
| 09 | | 38.7 | 39.0 | |
| ALL | 17.8 ± 15.6 | 30.7 ± 11.7 | 45.9 ± 12.5 | 49.2 |

TABLE 14

Food Intake Effect of Jojoba Seed Meal in Cats' Diet Before and After Weight Loss to Optimum Body Weight

| Cat | Diet Fed | Grams/kg Wt. Eaten (Avg ± SD) and in ( ) No. of Weeks on that Diet | | |
|---|---|---|---|---|
| | | Above Opt. Wt. | At Opt. Wt. | % Change |
| Jr | FC-1 | 12.90 ± 5.46 (2) | 14.86 ± 7.26 (4) | +15.2 |
| K8 | FC-2 | 10.94 ± 5.46 (7) | 11.30 ± 6.84 (4) | +3.3 |
| Merri | FC-1 | 11.98 ± 4.56 (2) | 11.10 ± 3.92 (4) | −7.3 |
| 47 | FC-2 | 8.07 ± 3.17 (6) | 8.22 ± 3.19 (4) | +1.9 |
| 48 | FC-2 | 10.70 ± 3.33 (3) | 9.52 ± 3.57 (4) | −11.0 |
| Avg. | FC-1 & 2 | 10.92 ± 1.83 (4 ± 2.35) | 11.00 ± 2.50 (4) | +0.4 ± 10.2 |

TABLE 15

Change in Amount Consumed and Body Weight of Cats Fed Jojoba Containing Diets

| CAT | On Diet FC-0 | | On Diet FC-1 | | On Diet FC-2 | | On Diet FC-3 | | On Diet FC-4 | |
|---|---|---|---|---|---|---|---|---|---|---|
| | | B. Wt | % Change In | | % Change In | | % Change In | | % Change In | |
| | g/kg Eaten | Change % | Amt Eaten | B. Wt/wk | Amt Eaten | B. Wt/wk | Amt Eaten | B. Wt/wk | Amt Eaten | B. Wt/wk |
| H04 | 14.6 | +0.3 | | | −29.0 | −0.1 | −47.1 | −5.4 | | |
| 46 | 12.7 | −0.3 | +11.2 | +2.0 | −47.7 | −3.7 | −51.5 | −2.4 | | |
| Jr | 23.4 | +0.6 | −39.3 | −0.5 | −48.4 | −5.0 | | | | |
| H02 | 19.7 | +1.0 | | | −18.1 | −0.6 | −58.2 | −2.4 | | |
| 47 | 9.3 | −0.6 | +35.8 | +1.2 | −12.6 | −1.5 | −16.0 | −1.6 | | |
| K8 | 15.6 | −0.4 | −2.5 | +2.8 | −29.1 | −1.5 | −50.3 | −2.7 | | |
| Merri | 14.0 | +1.8 | −17.0 | +1.0 | −27.7 | −2.2 | −51.7 | −1.8 | | |
| 48 | 14.4 | +1.3 | −12.3 | +1.0 | −25.2 | −0.9 | −37.0 | −0.4 | +49.2 | −2.3 |
| 55 | 12.2 | +0.3 | −20.2 | +0.1 | −35.3 | −0.6 | −57.4 | −3.1 | | |
| 42 | 15.3 | +0.2 | −25.5 | +0.1 | −24.9 | −0.3 | −50.6 | −2.0 | | |
| 09 | 9.5 | −0.2 | | | −38.7 | −2.1 | −39.0 | −3.1 | | |
| ALL | 14.6 | +0.3 | −8.7 | +1.0 | −30.5 | −1.7 | −45.9 | −2.5 | −49.2 | −2.3 |

TABLE 16

Individual Cat's Body Weight Changes When Fed Jojoba Containing Diets

| CAT | % of Opt Wt | | when fed | for ___ | Avg % Chg in | Conclusion and/or |
|---|---|---|---|---|---|---|
| | Begin[1] | End | diet | weeks[1] | wt/wk[1] | Comments |
| 35 | 113.3 | 104.0 | FC-0 | 9 | −0.93 | Not obese so omitted |
| H02 | 109.8 | 115.4 | FC-0 | 5 | +1.02 | During 14th week of study, |
| | 115.4 | 114.0 | FC-2 | 2 | −0.61 | became ill with and died |
| | 114.0 | 101.2 | FC-3 | 5 | −2.35 | of cardiomyopathy with no hepatic lipidosis. |
| 09 | 137.5 | 136.7 | FC-0 | 3 | −0.18 | Developed upper |
| | 136.7 | 128.4 | FC-3 | 2 | −3.11 | respiratory disease, |
| | 128.4 | 108.4 | FC-2 | 8 | −2.07 | treated and recovered |
| | 108.4 | 98.6 | FC-0 | 2* | −4.5 | during these 2 weeks but because cat was below optimum wt following recovery, it was removed from study. |
| K8 | 136.0 | 133.8 | FC-0 | 4 | −0.41 | |
| | 133.8 | 121.6 | FC-2 | 6 | −1.58 | |

TABLE 16-continued

Individual Cat's Body Weight Changes When Fed Jojoba Containing Diets

| CAT | % of Opt Wt Begin[1] | End | when fed diet | for weeks[1] | Avg % Chg in wt/wk[1] | Conclusion and/or Comments |
|---|---|---|---|---|---|---|
| | 121.6 | 107.3 | FC-3 | 5 | −2.44 | |
| | Developed upper resp. disease and treated. | | | 2 | −1.8 | |
| | 103.6 | 104.4 | FC-2 | 1 | +0.86 | |
| | 104.4 | 100.4 | FC-3 | 1 | −3.83 | *Jojoba in FC-1 too low for |
| | 100.4 | 106.2 | FC-1* | 2 | +2.84 | wt. maintenance. |
| | 106.2 | 98.7 | FC-2** | 4 | −1.83 | **Jojoba in FC-2 too high for wt. maintanence. |
| | FC-2 Avg: | | | | | |
| | 114.5 | 108.2 | FC-2 | 11 | −1.45 | |
| | FC-3 Avg: | | FC-3 | 6 | −2.67 | |
| | 113.0 | 103.8 | | | | |
| H04 | 111.0 | 114.0 | FC-0 | 9 | +0.31 | |
| | 114.0 | 102.0 | FC-3 | 2 | −5.38 | |
| | 102.0 | 101.5 | FC-2 | 4 | −0.12 | |
| Jr | 114.5 | 118.8 | FC-0 | 6 | +0.62 | |
| | 118.8 | 109.3 | FC-2 | 1 | −8.00 | |
| | 109.3 | 108.5 | FC-1 | 2 | −1.74 | |
| | 108.5 | 101.0 | FC-2 | 2 | −3.52 | |
| | 101.0 | 98.8 | FC-1 | 4 | −0.54 | |
| | FC-1 Avg: | | | | | |
| | 105.2 | 103.7 | FC-1 | 6 | −0.48 | |
| | FC-2 Avg: | | | | | |
| | 113.7 | 105.2 | FC-2 | 3 | −5.01 | |
| Merri | 110.7 | 118.9 | FC-0 | 4 | −1.62 | |
| | 118.9 | 113.6 | FC-2 | 1 | −4.49 | |
| | 113.6 | 113.6 | FC-1 | 2 | +3.01 | |
| | 113.6 | 113.8 | FC-2 | 1 | +3.23 | |
| | 113.8 | 98.3 | FC-3 | 8 | −2.00 | |
| | 98.3 | 101.9 | FC-1* | 4 | +0.77 | |
| | FC-1 Avg: | | | | | |
| | 105.8 | 107.8 | FC-1 | 6 | +1.51 | Jojoba in FC-1 may be too low for wt mtc. |
| | FC-2: | | | | | |
| | 116.3 | 113.7 | FC-2 | 2 | −2.15 | |
| 55 | 132.0 | 133.3 | FC-3 | 3 | +0.32 | |
| | 133.3 | 125.6 | FC-3 | 1 | −5.73 | |
| | 125.6 | 123.3 | FC-2 | 1 | −3.62 | |
| | 123.3 | 98.6 | FC-3 | 8 | −2.75 | |
| | 98.6 | 98.9 | FC-1 | 4 | +0.10 | |
| | FC-3 Avg: | | | | | |
| | 128.3 | 112.1 | FC-3 | 9 | −3.06 | |
| 42 | 123.0 | 123.8 | FC-3 | 3 | +3.23 | |
| | 123.8 | 118.0 | FC-3 | 2 | −2.35 | |
| | 118.0 | 117.3 | FC-2 | 2 | −3.32 | |
| | 117.3 | 100.5 | FC-3 | 8 | −1.89 | |
| | 100.5 | 100.8 | FC-1 | 4 | +0.10 | |
| | FC-3 Avg: | | | | | |
| | 120.6 | 109.3 | FC-3 | 10 | −1.98 | |
| 46 | 117.0 | 114.0 | FC-1 | 9 | −0.28 | *Jojoba in FC-2 too high |
| | 114.0 | 100.8 | FC-3 | 5 | −2.42 | for wt mtc. |
| | 100.8 | 93.4 | FC-2 | 2 | −3.72 | **Jojoba in FC-1 too low |
| | 93.4 | 101.0 | FC-1** | 4 | +2.01 | for wt mtc. |
| 47 | 121.3 | 118.5 | FC-0 | 4 | −0.56 | |
| | 118.5 | 108.9 | FC-2 | 6 | −1.40 | |
| | 108.9 | 100.5 | FC-3 | 5 | −1.59 | |
| | 100.5 | 106.9 | FC-1* | 5 | +1.24 | *Jojoba in FC-1 too low for |
| | 106.9 | 100.5 | FC-2** | 4 | −1.52 | wt mtc. **Jojoba FC-2 too high for wt mtc. |
| | FC-2 Avg: | | | | | |
| | 112.7 | 104.7 | FC-2 | 10 | −1.45 | |
| 48 | 114.6 | 120.4 | FC-0 | 4 | +1.25 | |
| | 120.4 | 115.2 | FC-2 | 1 | −4.32 | |

TABLE 16-continued

Individual Cat's Body Weight Changes When Fed Jojoba Containing Diets

| CAT | % of Opt Wt Begin[1] | End | when fed diet | for ___ weeks[1] | Avg % Chg in wt/wk[1] | Conclusion and/or Comments |
|---|---|---|---|---|---|---|
| | 115.2 | 117.6 | FC-1 | 2 | +1.04 | |
| | 117.6 | 118.0 | FC-2 | 2 | +0.18 | |
| | 118.0 | 114.0 | FC-3 | 5 | −0.67 | |
| | 114.0 | 105.0 | FC-4 | 2 | −4.03 | |
| | 105.0 | 104.6 | FC-3 | 4 | −0.39 | |
| | 104.6 | 98.6 | FC-4 | 4 | −1.46 | |
| | 98.8 | 96.0 | FC-2* | 4 | −0.65 | |
| | FC-2 Avg: | | | | | Jojoba in FC-2 too high |
| | 112.2 | 109.7 | FC-2 | 7 | −0.94 | for wt mtc. |
| | FC-3 Avg: | | | | | |
| | 111.5 | 109.3 | FC-3 | 9 | −0.41 | |
| | FC-4 Avg: | | | | | |
| | 109.3 | 101.8 | FC-4 | 6 | −2.32 | |

[1]First week Diet FC-0 was feed excluded.

TABLE 17

Average Body Weight Changes in Cats Fed Diets Containing Different Amounts of Jojoba Seed Meal

| | % of Opt WT Begin | End | Weeks Fed | % Change in B. wt/wk | Conclusions and/or Comments |
|---|---|---|---|---|---|
| DIET FC-0 (0% Jojoba Meal)(n = 12) | | | | | |
| Mean | 120.1[1] | 121.0[1] | 5.3[1] | +0.30[1] | 3 of 32 cats gained wt (1 to 1.8%/wk), 1 lost wt (0.9%/wk) so was omitted from the study and 8 maintained wt (±0.6%/wk) on FC-0. |
| S.D. | ±10.0 | ±9.6 | ±2.4 | ±0.37 | |
| Min. | 109.5 | 104.0 | 3 | −0.9 | |
| Max. | 137.5 | 136.7 | 9 | +1.8 | |
| DIET FC-1 (2% Jojoba Meal)(n = 8) | | | | | |
| Mean | 102.5 | 105.4 | 4.1 | ±0.98 | 4 of 8 cats gained wt (1.0 to 2.8%/wk) and 4 maintained wt (±0.5 to −0.1%/wk) when fed FC-1. |
| S.D. | ±6.4 | ±5.9 | ±1.6 | ±1.09 | |
| Min. | 93.3 | 98.9 | 2 | −0.1 | |
| Max. | 115.2 | 117.6 | 6 | +2.8 | |
| DIET FC-2 (4% Jojoba Meal)(n = 11) | | | | | |
| Mean | 114.5 | 109.0 | 4.9 | −1.68 | 9 of 11 cats lost wt (0.6 to 5.0%/wk), 1 lost slightly (0.3%/wk) and needed FC-1 for wt maintenance (±0.1%/wk), and 1 needed FC-2 for wt. mtc. (0.1%/wk) |
| S.D. | ±8.3 | ±8.1 | ±3.5 | ±1.51 | |
| Min. | 100.8 | 93.4 | 1 | −0.1 | |
| Max. | 128.4 | 123.3 | 11 | −5.0 | |
| DIET FC-3 (8% Jojoba Meal)(n = 11) | | | | | |
| Mean | 117.9 | 106.6 | 5.5 | −.260 | 9 cats lost 1.5 to 3.8%/wk when fed FC-3; 1** lost 5.4%/wk but was only fed FC-3 for 2 weeks; and 1** lost only 0.4%/wk over 9 weeks so was fed FC-4 on which it lost 2.3%/wk. |
| S.D. | ±8.3 | ±8.5 | ±3.1 | ±1.32 | |
| Min. | 104.4 | 98.0 | 2 | −0.4% | |
| Max. | 136.7 | 128.4 | 10 | −5.4** | |
| DIET FC-4 (12% Jojoba Meal)(n = 1) (Cat. #48) | | | | | |
| Mean | 109.3 | 101.8 | 6 | −2.32 | This cat lost only 0.4%/wk when fed FC-3 for 9 weeks but 2.3%/wk when fed FC-4. It gained wt on FC-1 (1.0%/wk) but lost wt on FC-2 (0.6%/wk). |
| S.D. | | | | ±1.55 | |
| Min. | 103.6 | 98.6 | | −0.6 | |
| Max. | 108.8 | 105.0 | | −4.6 | |

[1]Excludes first week Diet FC-0 was fed.

TABLE 18

Hematology and Serum Chemistry Results in Cats Fed Jojoba Seed Meal

| | DATE | | | | | | | | Lab Normal |
|---|---|---|---|---|---|---|---|---|---|
| | 4/9 | 3/23 | 3/23 | 4/23 | 6/22 | 4/2 | 6/4 | 6/8 | |
| | CAT | | | | | | | | |
| | Crys | Mryw | Jr | Jr | Jr | H02 | H02 | H02 | Range |
| ALT (IU/L) | 29 | 150 | 55 | 86 | 82 | 53 | 31 | 21 | 2–98 |
| Albumie (g/dl) | 4.6 | 3.8 | 3.9 | 3.9 | 3.9 | 3.9 | 4.1 | 3.5 | 2.5–4.3 |
| Alk Phos (IU/L) | 31 | 63 | 62 | 60 | 52 | 16 | 23 | 32 | 0–50 |
| AST(IU/L) | 16 | 39 | 19 | 39 | 18 | 21 | 17 | 16 | 6–36 |
| Calcium (mg/dl) | 9.2 | 10.1 | 9.3 | 9.8 | 10.0 | 9.4 | 8.9 | 8.2 | 7.8–12.2 |
| Creatine (mg/dl) | 4.2 | 1.4 | 0.8 | 1.1 | 0.8 | 1.2 | 1.1 | 0.9 | 0.9–2.6 |
| Glucose (mg/dl) | 116 | 89 | 93 | 94 | 131 | 91 | 170 | 196 | 57–117 |
| GGT-IU/L | 0.9 | 0.2 | 0.7 | 2.4 | 2.5 | 1.5 | 0.4 | 0.0 | 0–5.1 |
| Phosphorus (mg/dl) | 6.6 | 4.5 | 4.8 | 4.1 | 4.5 | 4.7 | 6.3 | 5.8 | 3.2–7.0 |
| Total Protein (g/dl) | 8.1 | 7.6 | 7.7 | 8.1 | 7.1 | 7.5 | 6.5 | 5.7 | 6.1–9.1 |
| BUN (mg/dl) | 70.6 | 37.4 | 18.5 | 16.8 | 24.9 | 17.5 | 20.2 | 15.5 | 13–35 |
| Sodium (meq/l) | 156 | 156 | 158 | 158 | 160 | 159 | 155 | 168 | 152–162 |
| Potassium (meq/l) | 3.9 | 4.7 | 5.2 | 3.9 | 4.8 | 4.9 | 4.7 | 3.3 | 3.4–5.8 |
| Chloride (meq/l) | 137 | 120 | 123 | 116 | 123 | 123 | 116 | 126 | 118–128 |
| Tot. Bilirubin (mg/dl) | 0.3 | 0.4 | 0.3 | 0.2 | 0.1 | 0.2 | 0.3 | 0.2 | 0–1.0 |
| Globulin (g/dl) | 3.5 | 3.8 | 3.8 | 4.2 | 3.2 | 3.6 | 2.4 | 2.2 | |
| A/G/Ratio | 1.31 | 1.00 | 1.03 | 0.93 | 1.22 | 1.08 | 1.71 | 1.59 | |
| Cholesterol (mg/dl) | 133 | 168 | 142 | 157 | 139 | 101 | 156 | 177 | |
| T4 (ug/dl) | 1.50 | 1.20 | 3.70 | — | 4.23 | 3.00 | — | 0.80 | 0.8–4.0 |
| WBC ($10^3/mm^3$) | 8.4 | 20.0 | 27.3 | 8.5 | 12.2 | 12.3 | — | 24.6 | 3.1–23.4 |
| RBC ($10^6/mm^3$) | 7.67 | 9.18 | 8.50 | 8.02 | 6.82 | 5.75 | — | 5.81 | 5.1–11.4 |
| Hemoglobin (g/dl) | 12.6 | 13.3 | 12.8 | 11.8 | 10.3 | 9.3 | — | 10.5 | 8.9–16.9 |
| Hematocrit (%) | 37.7 | 37.2 | 36.5 | 34.5 | 31.1 | 27.4 | — | 30.4 | 26.2–51.2 |
| MCV ($um^2$) | 49.1 | 40.5 | 42.9 | 43.3 | 45.6 | 47.6 | — | 52.4 | 39.7–54.7 |
| MCH (uug) | 16.4 | 14.5 | 15.1 | 14.7 | 15.1 | 16.2 | — | 18.1 | 13.2–18.2 |
| MCHC (%) | 33.4 | 35.8 | 35.1 | 34.0 | 33.1 | 33.9 | — | 34.5 | 31–36 |
| Platelets ($10^3/mm^3$) | 265 | 397 | 589 | 369 | 301 | 175 | — | 154 | 40–402 |

| | DATE | | | | | | | | Lab Normal |
|---|---|---|---|---|---|---|---|---|---|
| | 4/2 | 6/22 | 6/9 | 9/10 | 9/17 | 9/24 | 10/1 | | |
| | CAT | | | | | | | | |
| | H04 | H04 | 09 | 48 | 48 | 48 | 48 | | Range |
| ALT (IU/L) | 25 | 23 | 22 | 9 | — | — | — | — | 2–98 |
| Albumie (g/dl) | 3.1 | 3.3 | 4.3 | 3.5 | — | — | — | — | 2.5–4.3 |
| Alk Phos (IU/L) | 5 | 13 | 43 | 14 | — | — | — | — | 0–50 |
| AST(IU/L) | 17 | 18 | 20 | 12 | — | — | — | — | 6–36 |
| Calcium (mg/dl) | 9.1 | 9.5 | 9.6 | 8.8 | — | — | — | — | 7.8–12.2 |
| Creatine (mg/dl) | 1.3 | 1.3 | 1.9 | 1.0 | — | — | — | — | 0.9–2.6 |
| Glucose (mg/dl) | 125 | 101 | 107 | 99 | — | — | — | — | 57–117 |
| GGT-IU/L | 0.9 | 1.5 | 0.6 | 0.7 | — | — | — | — | 0–5.1 |
| Phosphorus (mg/dl) | 3.5 | 4.0 | 5.5 | 4.8 | — | — | — | — | 3.2–7.0 |
| Total Protein (g/dl) | 6.1 | 6.9 | 8.3 | 6.6 | — | — | — | — | 6.1–9.1 |
| BUN (mg/dl) | 19.0 | 20.2 | 38.1 | 17.9 | — | — | — | — | 13–35 |
| Sodium (meq/l) | 153 | 156 | 159 | 150 | — | — | — | — | 152–162 |
| Potassium (meq/l) | 4.2 | 4.7 | 4.4 | 4.7 | — | — | — | — | 3.4–5.8 |
| Chloride (meq/l) | 120 | 121 | 119 | 120 | — | — | — | — | 118–128 |
| Tot. Bilirubin (mg/dl) | 0.2 | 0.2 | 0.4 | 0.1 | — | — | — | — | 0–1.0 |
| Globulin (g/dl) | 3.0 | 3.6 | 4.0 | 3.1 | — | — | — | — | |
| A/G/Ratio | 1.03 | 0.92 | 1.08 | 1.13 | — | — | — | — | |
| Cholesterol (mg/dl) | 109 | 104 | 130 | — | — | — | — | — | |
| T4 (ug/dl) | 0.80 | 1.25 | — | — | 2.00 | — | — | — | 0.8–4.0 |
| WBC ($10^3/mm^3$) | 26.2 | 26.0 | 8.4 | 17.0 | 16.8 | 16.2 | 11.7 | — | 3.1–23.4 |
| RBC ($10^6/mm^3$) | 9.61 | 7.50 | 6.56 | 4.35 | 4.87 | 4.09 | 4.89 | — | 5.1–11.4 |
| Hemoglobin (g/dl) | 14.7 | 12.9 | 10.7 | 8.1 | 8.2 | 6.9 | 8.0 | — | 8.9–16.9 |
| Hematocrit (%) | 45.4 | 37.2 | 31.6 | 23.8 | 26.6 | 21.7 | 25.4 | — | 26.2–51.2 |
| MCV ($um^2$) | 47.2 | 49.6 | 48.1 | 54.8 | 54.6 | 53.0 | 52.4 | — | 39.7–54.7 |
| MCH (uug) | 15.3 | 17.2 | 16.3 | 18.6 | 16.8 | 16.9 | 16. | — | 13.2–18.2 |
| MCHC (%) | 32.4 | 34.7 | 33.9 | 34.0 | 30.8 | 31.8 | 31. | — | 31–36 |
| Platelets ($10^3/mm^3$) | 326 | 470 | 334 | 187 | 134 | 175 | 192 | — | 40–402 |

TABLE 19

Comparison of Cat and Dog Food Intake and Body weight Changes with Jojoba Consumption

| | Jojoba Seed Meat In Diet - % | Simmondsin Activity in Diet - % | Food Intake g/kg/day & % Decrease | Body Wt Change %/wk |
|---|---|---|---|---|
| Cats | 0 | 0 | 14.6 g/kg/d | +0.3 |
| Dogs | 0 | 0 | 28.0 g/kg/d | +2.7 |
| Cats | 2 | 0.12 | −8.7% | +1.0 |
| Cats | 4 | 0.24 | −30.7% | −1.7 |
| Dogs | 4.5 | 0.27–0.36 | −25.0% | +0.05 |
| Cas | 5 | 0.49 | −45.9% | −2.6 |
| Dogs | 6 | 0.48–0.65 | −40.7% | −2.2 |

It therefore can be seen that the invention accomplishes all of its stated objectives.

What is claimed is:

1. A method of weight reduction and weight maintenance in a cat comprising: feeding cat food containing dry matter to a cat, said cat food including a simmondsin component, a simmondsin analogue, or a mixture thereof, sufficient to provide in the cat food dry matter pure simmondsin of at least 0.24% by weight until the cat reaches its target weight; and then feeding the cat a simmondsin component, a simmondsin analogue, or a mixture thereof, sufficient to provide the cat pure simmondsin within the range from about 0.1% by weight of cat food dry matter mix to about 0.18% by weight of cat food dry matter mix to maintain the cat's target weight.

2. A method of weight reduction and weight maintenance according to claim 1 wherein the simmondsin component is defatted jojoba seed meal.

3. A method of weight reduction and weight maintenance according to claim 1 wherein the simmondsin component comprises 0.49% or less by weight of the cat food dry matter.

4. A method of weight reduction and weight maintenance according to claim 1 wherein the cat reduces its food intake by at least 30.5% (±11.15%), over a period of time that is at least two weeks.

5. A method of weight reduction and weight maintenance in a cat comprising:

feeding cat food containing dry matter to a cat, said cat food including a simmondsin component, a simmondsin analogue, or a mixture thereof, sufficient to provide in the cat food dry matter pure simmondsin of at least 0.18% by weight until the cat reaches its target weight; and then feeding the cat a simmondsin component, a simmondsin analogue, or a mixture thereof, sufficient to provide the cat pure simmondsin within the range from about 0.1% by weight of cat food dry matter mix to about 0.18% by weight of cat food dry matter mix to maintain the car's target weight.

6. A method of weight reduction and weight maintenance according to claim 5 wherein the simmondsin component is defatted jojoba seed meal.

7. A method of weight reduction and weight maintenance according to claim 5 wherein the simmondsin component comprises 0.24%, but more than 0.12%, by weight of the cat food dry matter.

* * * * *